(12) United States Patent
Nadkarni et al.

(10) Patent No.: US 9,040,695 B2
(45) Date of Patent: May 26, 2015

(54) ACID ADDITION SALTS OF RISPERIDONE AND PHARMACEUTICAL COMPOSITIONS THEREOF

(75) Inventors: Sunil Sadanand Nadkarni, Gandhinagar (IN); Arunkumar Gupta, Gandhinagar (IN); Manish Parikh, Gandhinagar (IN); Jaya Abraham, Gandhinagar (IN); Vivek Mishra, Gandhinagar (IN)

(73) Assignee: TORRENT PHARMACEUTICALS LIMITED (IN)

( * ) Notice: Subject to any disclaimer, the term of this patent is extended or adjusted under 35 U.S.C. 154(b) by 0 days.

(21) Appl. No.: 14/114,379

(22) PCT Filed: Apr. 25, 2012

(86) PCT No.: PCT/IB2012/052065
§ 371 (c)(1), (2), (4) Date: Oct. 28, 2013

(87) PCT Pub. No.: WO2012/147035
PCT Pub. Date: Nov. 1, 2012

(65) Prior Publication Data
US 2014/0045864 A1    Feb. 13, 2014

(30) Foreign Application Priority Data
Apr. 26, 2011 (IN) .................. 1310/MUM/2011

(51) Int. Cl.
| | |
|---|---|
| *C07D 401/14* | (2006.01) |
| *C07D 403/14* | (2006.01) |
| *A61K 31/506* | (2006.01) |
| *A61P 25/18* | (2006.01) |
| *C07D 471/04* | (2006.01) |
| *A61K 45/06* | (2006.01) |

(52) U.S. Cl.
CPC .............. *C07D 471/04* (2013.01); *A61K 45/06* (2013.01); *A61K 31/506* (2013.01); *C07D 403/14* (2013.01); *C07D 401/14* (2013.01)

(58) Field of Classification Search
CPC ..... C07D 401/14; A61K 45/06; A61K 31/506
USPC ..................................... 544/282; 514/259.41
See application file for complete search history.

(56) References Cited

U.S. PATENT DOCUMENTS

| 5,612,346 A | * | 3/1997 | Mesens et al. ........... 514/259.41 |
| 5,723,467 A | * | 3/1998 | Mesens et al. ........... 514/259.41 |

FOREIGN PATENT DOCUMENTS

EP    0569096 A1    5/1993

OTHER PUBLICATIONS

Vippagunta et al., Advanced Drug Delivery Reviews 48: 3-26, 2001.*
Ulrich J. Kirk-Othmer Encyclopedia of Chemical Technology, John Wiley & Sons, Inc, pp. 1-7, 2002.*
International Search Report and Written Opinion for International Application No. PCT/IB2012/052065; Date of Mailing: Sep. 21, 2012; 10 pages.

* cited by examiner

*Primary Examiner* — Venkataraman Balasubramanian
(74) *Attorney, Agent, or Firm* — Cantor Colburn LLP

(57) ABSTRACT

The present invention relates to a novel acid addition salt of risperidone, wherein acid counterion is selected from the group consisting of pamoic acid, caproic acid, cypionic acid, decanoic acid, camphor sulfonic acid, enanthic acid, palmitic acid, fusidic acid, gluceptic acid, gluconic acid, lactobionic acid, lauric acid, levulinic acid and valeric acid, a process for the preparation and pharmaceutical composition comprising the same. Further, the invention relates to the use of said pharmaceutical composition comprising the acid addition salt of risperidone in the treatment of patient suffering from psychotic disorders.

12 Claims, 3 Drawing Sheets

ACID ADDITION SALTS OF RISPERIDONE AND PHARMACEUTICAL COMPOSITIONS THEREOF

Figure 1:
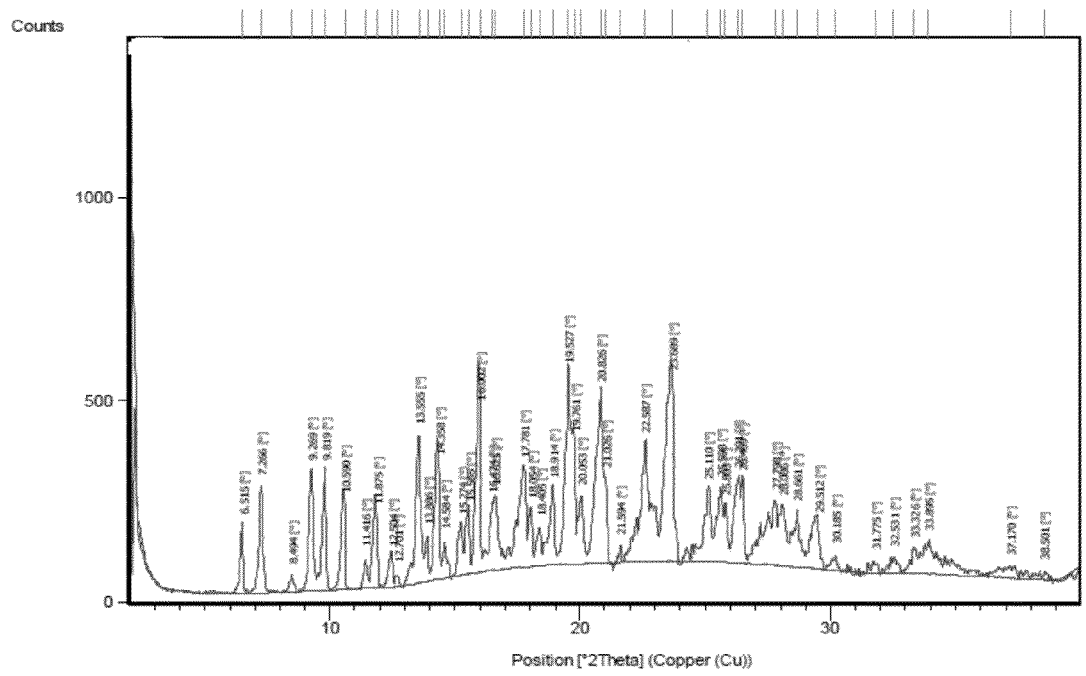

This is the U.S. national stage of application No. PCT/IB2012/052065, filed on 25 Apr. 2012. Priority under 35 U.S.C. §119(a) and 35 U.S.C. §365(b) is claimed from Indian Application No. 1310/MUM/2011, filed 26 Apr. 2011, the disclosure of which is also incorporated herein by reference.

FILED OF THE INVENTION

The present invention relates to a novel acid addition salt of risperidone, wherein acid counterion is selected from the group consisting of pamoic acid, caproic acid, cypionic acid, decanoic acid, camphor sulfonic acid, enanthic acid, palmitic acid, fusidic acid, gluceptic acid, gluconic acid, lactobionic acid, lauric acid, levulinic acid and valeric acid, a process for the preparation and pharmaceutical composition comprising the same. Further, the invention relates to the use of said pharmaceutical composition comprising the acid addition salt of risperidone in the treatment of patient suffering from psychotic disorders.

BACKGROUND OF THE INVENTION

Risperidone (also known as 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one and marketed under the trade name RISPERDAL®) is an atypical antipsychotic medication. The chemical structure of risperidone is shown in formula (I).

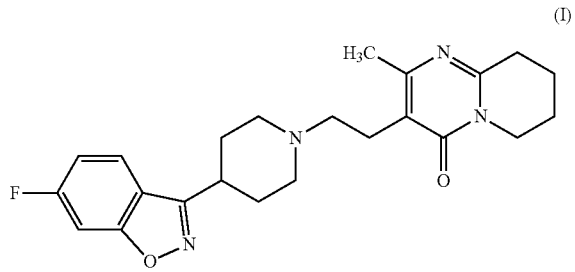 [SMILES: Cc1nc2n(c(=O)c1CCN1CCC(c3noc4cc(F)ccc34)CC1)CCCC2]

Risperidone is most often used to treat delusional psychosis (including schizophrenia), also risperidone finds utility in treatment of some forms of bipolar disorder, psychotic depression, obsessive-compulsion disorder, and Tourette syndrome. Risperidone is also used in low doses for treating autistic spectrum disorders. Risperidone's therapeutic activity in schizophrenia is believed to be mediated through a combination of dopamine Type 2 (D2) and serotonin Type 2 (5HT2) receptor antagonism.

Currently, Risperidone is available as immediate release tablets/syrups as well as long acting injectable. Long acting injections has gained acceptance with the medical fraternity owing to decreased incidences of hospitalization in patients with schizophrenia. The commercial sustained release product of an atypical psychotic is Risperdal® Consta, marketed by Janssen. Risperdal® consta is an intramuscular microsphere formulation and is intended to deliver therapeutic levels of risperidone for two weeks. However due to inherent lag phase of microsphere product, the patient is required to supplement the first 21 days of Risperdal® consta treatment with daily doses of risperidone by oral therapy. Approximately three weeks after a single intramuscular injection of Risperdal® consta and concurrent daily doses of oral risperidone, the microparticles release sufficient risperidone in the systemic circulation so that the patient can discontinue supplementation with daily doses of oral therapy.

The primary limitation of micro spheres used in sustained-release delivery systems is, typically the limited amount of drug that can be entrapped in the dosage form with complex manufacturing process & controls & high costs. Further, the size of the gauze of injection needle is limited by the discomfort of the patient.

Other sustained-release delivery systems such as solid, biodegradable rods or nondegradable reservoir typically require surgical implantation. Furthermore, for the non-degradable delivery systems, a second surgical procedure is required to remove the empty reservoir.

The afore-mentioned delivery systems require use of expensive excipients, special device and need specifically designed processes. Hence making them very expensive and increase cost of therapy.

EP-0,196,132 discloses the compound 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one, that is known generally as risperidone and is a potent antipsychotic. The same patent also discloses the acid addition salt of risperidone for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

U.S. Pat. No. 5,612,346 disclose the pamoate acid addition salt of Risperidone having melting point of 269.2° C. and a process for the preparation thereof. The '346 patent also discloses a long acting pharmaceutical formulation of pamoate salt of risperidone. The poorly soluble salt form is suspended in the aqueous vehicle and was shown effective for over 2 week period in dogs. However, this product is not available in clinic. Olanzapine Pamoate (Zyprexa Relprevv) is available as long acting injectable formulation given IM for human use for the treatment of atypical antipsychotic disorders, is another example where poorly soluble salt form is suspended in aqueous vehicle. There is no lag phase observed in this kind of system and thus oral supplement are not required after first depot administration unlike the current marketed preparation Risperdal® consta.

WO 2004094414 discloses water soluble salt of risperidone in solid state having a water solubility of at least 10 mg/ml. The salt preferably has solubility within the range of 20 to 200 mg/ml. The salt is preferably a pharmaceutically acceptable acid addition salt include hydrochloric acid, methane sulfonic acid, tartaric acid, maleic acid, malic acid, ethane disulfonic acid, lactic acid, acetic acid, and mandelic acid.

Risperidone acid addition salts known in art are either not suitable for long acting formulation because of their physical characteristics or requires high drug loading due to their high molecular weight to achieve desirable drug concentration for long lasting effect.

There still exists need for acid addition salt of risperidone that has desired physical characteristics that are distinct from the previously disclosed and prepared salt of risperidone.

The discovery of new salt forms of a pharmaceutically useful compound risperidone provides a new opportunity to design drug delivery systems with improved pharmacokinetic profile with constant plasma concentrations with minimum peak & trough ratio, improved safety profile, ranging from few days to months. The salts would be useful for designing drug delivery system from immediate release to long acting dosage forms by different routes of administration We have now surprisingly and unexpectedly discovered novel acid addition salts of risperidone, which are different from the known salt of risperidone disclosed in said prior art.

SUMMARY OF THE INVENTION

In one aspect, the present invention provides a novel acid addition salt of risperidone, wherein acid counterion is selected from the group consisting of caproic acid, cypionic acid, decanoic acid, camphor sulfonic acid, enanthic acid, palmitic acid, fusidic acid, glucepctic acid, gluconic acid, lactobionic acid, lauric acid, levulinic acid and valeric acid.

In yet another aspect, the present invention provides Risperidone hemipamoate.

In yet another aspect, the present invention provides crystalline Risperidone hemipamoate.

In another aspect, the present invention further encompasses a process for the preparation of novel acid addition salt of risperidone, which comprises:
  a) reacting risperidone with an acid counterion in suitable solvent to form a risperidone salt;
  b) removing said suitable solvent, thereby isolating risperidone salt; and
  c) optionally purifying the obtained risperidone salt.

In yet another aspect, the acid addition salt of risperidone according to present invention may be in solid state or in a dissolved or liquid form.

In yet another aspect, the present invention provides pharmaceutical compositions comprising a therapeutically effective amount of an acid addition salt of the risperidone or mixtures thereof according to the present invention, and one or more pharmaceutically acceptable excipients.

In yet another aspect, the present invention provides pharmaceutical compositions comprising the acid addition salt of risperidone prepared according to the processes of the present invention in any of its embodiments and one or more pharmaceutically acceptable excipients.

In yet another aspect, the present invention further encompasses a process for preparing a pharmaceutical composition comprising combining any one of the polymorphic forms of risperidone acid addition salts prepared according to processes of the present invention in any of its embodiments, with one or more pharmaceutically acceptable excipients.

In yet another aspect, the present invention provides long acting formulation comprising a therapeutically effective amount of any one of the acid addition salt of risperidone or polymorphic form or mixtures thereof according to present invention, and one or more pharmaceutically acceptable excipients with duration of drug release from about 7 days to 6 months.

In yet another aspect, the present invention provides long acting formulation comprising a therapeutically effective amount of any one of the acid addition salt of risperidone or polymorphic form or mixtures thereof according to present invention, suspended in biocompatible vehicle suitable for injection or polymeric vehicle suitable for injection.

In yet another aspect, the present invention provides long acting formulation comprising a therapeutically effective amount of any one of the acid addition salt of risperidone or polymorphic form or mixtures thereof according to present invention, suspended in buffered aqueous vehicle suitable for injection.

In yet another aspect, the present invention provides long acting formulation comprising a therapeutically effective amount of any one of the acid addition salt of risperidone salt or polymorphic form or mixtures thereof of according to present invention, suspended in oily vehicle suitable for injection.

In yet another aspect, the present invention provides long acting formulation comprising a therapeutically effective amount of any one of the acid addition salt of risperidone or polymorphic form or mixtures thereof according to present invention, also may be included in different delivery systems like solid implants, insitu implants, insitu microparticles, liposomal or may be linked to any carrier systems like dendrimers.

In yet another aspect, the present invention provides method for treatment of atypical psychotic disorder by administering long acting formulation comprising a therapeutically effective amount of any one of the acid addition salt of risperidone or polymorphic form or mixtures thereof according to present invention, suspended in biocompatible vehicle suitable for injection.

In yet another aspect, the present invention provides long acting formulation comprising a therapeutically effective amount of risperidone hemipamoate or polymorphic form or mixtures thereof and one or more pharmaceutically acceptable excipients with duration of drug release from about 7 days to 6 months.

In yet another aspect, the present invention provides long acting formulation comprising a therapeutically effective amount of risperidone hemipamoate or polymorphic form or mixtures thereof, suspended in biocompatible vehicle suitable for injection or polymeric vehicle suitable for injection.

In yet another aspect, the present invention provides long acting formulation comprising a therapeutically effective amount of risperidone hemipamoate or polymorphic form or mixtures thereof, suspended in buffered aqueous vehicle suitable for injection.

In yet another aspect, the present invention provides long acting formulation comprising a therapeutically effective amount of risperidone hemipamoate or polymorphic form or mixtures thereof, suspended in oily vehicle suitable for injection.

In yet another aspect, the present invention provides method for treatment of atypical psychotic disorder by administering long acting formulation comprising a therapeutically effective amount of risperidone hemipamoate or polymorphic form or mixtures thereof, prepared according to present invention.

BRIEF DESCRIPTION OF THE ACCOMPANYING DRAWINGS

FIG. 1: This figure indicates powder X-ray diffraction pattern of crystalline form T1 of risperidone hemipamoate obtained according to the instant invention.

Figure 2:
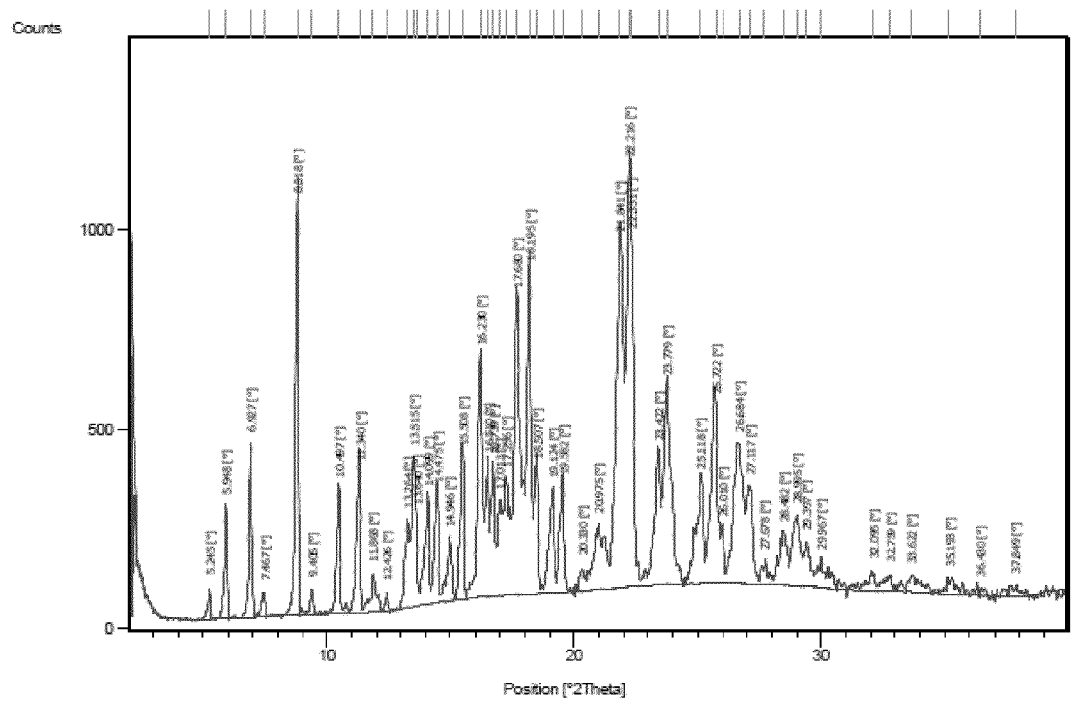

FIG. 2: This figure indicates powder X-ray diffraction pattern of crystalline form T2 of risperidone hemipamoate obtained according to the instant invention.

Figure 3:
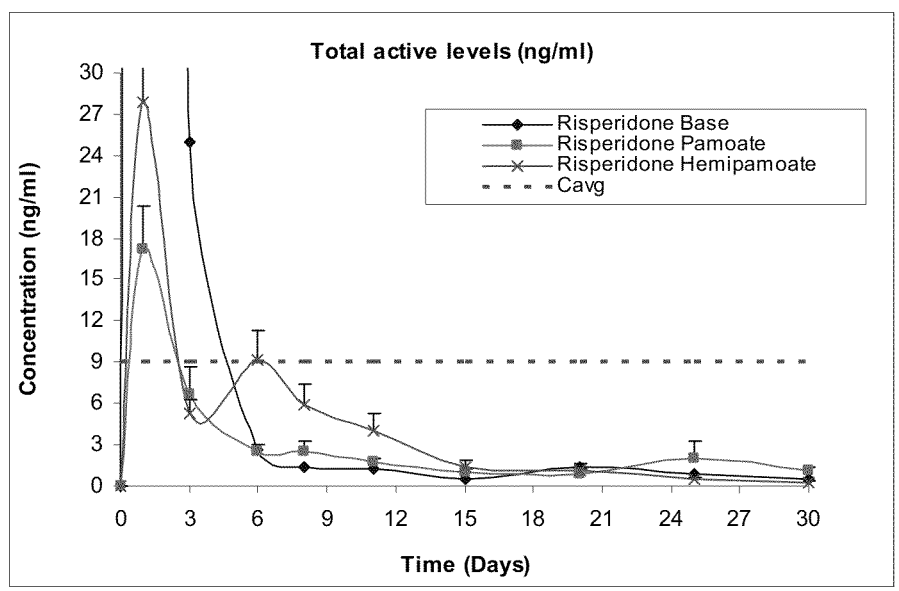

FIG. 3: This figure indicates comparative pharmacokinetic profile of Risperidone, Risperidone pamoate and Risperidone hemipamoate suspension after IM administration in wistar rats.

DETAILED DESCRIPTION OF THE INVENTION

The use of the terms "a" and "an" and "the" and similar referents in the context of describing the invention are to be construed to cover both the singular and the plural, unless otherwise indicated herein or clearly contradicted by context.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

As used herein, the term "risperidone" refers to the 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one i.e. compound of formula (I).

As used herein, the term "caproic acid" refers to the hexanoic acid.

As used herein, the term "cypionic acid" refers to the 3-cyclopentylpropionic acid.

As used herein, the term "enanthic acid" refers to the heptanoic acid.

As used herein, the term "fusidic acid" refers to the compound having a following structural formula.

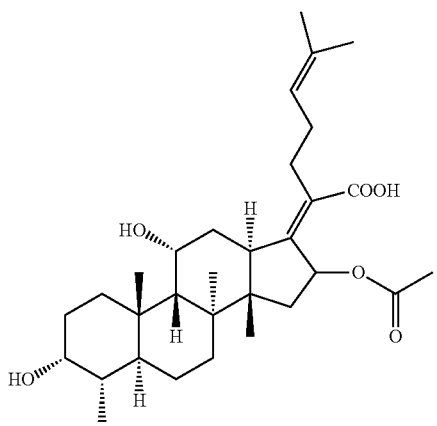

As used herein, the term "gluceptic acid" refers to the 2,3,4,5,6,7-hexahydroxyheptanoic acid.

As used herein, the term "gluconic acid" refers to the 2,3,4,5,6-pentahydroxyhexanoic acid.

As used herein, the term "lactobionic acid" refers to the compound having a following structural formula.

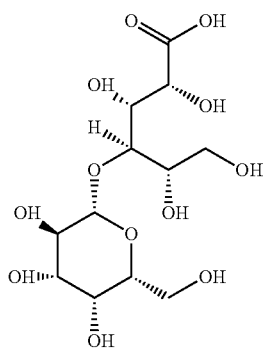 [SMILES: O=C(O)[C@H](O)[C@@H](O)[C@H](O[C@@H]1O[C@H](CO)[C@H](O)[C@H](O)[C@H]1O)[C@@H](O)CO]

As used herein, the term "lauric acid" refers to the dodecanoic acid.

As used herein, the term "levulinic acid" refers to the 4-oxopentanoic acid.

As used herein, the term "valeric acid" refers to the pentanoic acid.

As used herein, the term "palmitic acid" refers to the hexadecanoic acid.

A "salt" of risperidone means a mixture of ionic risperidone and acid counter-ion (s).

As used herein, the term "risperidone hemipamoate" refers to the Pamoate acid addition salt of risperidone, wherein ratio of risperidone to pamoic acid is 2:1.

The term "a therapeutically effective amount" as used herein refers the amount of a risperidone acid addition salt that, when administered to a patient for treating a disease, is sufficient to effect such treatment for the disease. The "therapeutically effective amount" will vary depending on the nature of acid addition salt, mode of administration, the disease and its severity and the age, weight, etc., of the patient to be treated.

In acid addition salt of risperidone according to the present invention, the risperidone is typically protonated on one or more nitrogen atoms to have one or more positive charges while the acid counter-ion (s) has one or more off-setting negative charges. The ions can be in a fixed spatial relationship as in a crystal lattice or in an unfixed relationship up to and including a random relationship. Further, the dissolved ions may have some degree of association or the ions can be completely dissociated.

In preferred embodiment, the acid addition salt of risperidone according to the present invention can be obtained in a solid state. Such solid state form can be useful for handling and/or purification as well as for making a solid state dosage form. The solid state can be crystalline or non-crystalline. When crystalline, it may occur in one or more polymorphic modifications.

Further, the solid state form, especially a crystalline form, can be a solvated form, including a hydrated form, or an anhydrous form. Non-crystalline forms can be amorphous forms as well as dispersed forms such as molecular dispersions, optionally within a solid matrix material.

Accordingly, acid addition salts of risperidone as described herein above encompasses all of the above states and forms, unless specifically limited, and are not necessarily in a solid state.

The solid state salt is preferably in isolated form; i.e. substantially separated from solvent, such as by filtration or heating, etc., and substantially free from other compounds such as synthetic precursors and/or side products. The solid state salt, whether isolated or not, preferably has a purity of at least 70%, more typically at least 90%, more preferably at least 95%, still more preferably at least 99%, wherein the percentages are based on weight.

In the risperidone acid addition salt, the ratio of risperidone ion to acid counter-ion can vary depending generally upon the acid counter-ion and the method of formation. This is because risperidone has more than one nitrogen atom that is susceptible to protonation and also many useful acids have more than one proton susceptible of protonating the risperidone base. Hence, risperidone may form various types of acid additions salts even with one acid of the present invention. Generally the molar amount of counter-ion per one mole of risperidone is in the range of 0.5 to 2, but is not limited thereto.

The present invention may, however, be embodied in many different forms and should not be construed as limited to the aspects set forth herein. In addition and as will be appreciated by one of skill in the art, the invention may be embodied as a method, system or process.

In general, the present invention provides a novel acid addition salt of risperidone, wherein acid counterion is selected from the group consisting of caproic acid, cypionic acid, decanoic acid, camphor sulfonic acid, enanthic acid, palmitic acid, fusidic acid, gluceptic acid, gluconic acid, lactobionic acid, lauric acid, levulinic acid and valeric acid.

The present invention further encompasses a process for the preparation of novel acid addition salt of risperidone, which comprises:
a) reacting risperidone with an acid counterion in suitable solvent to form a risperidone salt;
b) removing said suitable solvent, thereby isolating risperidone salt; and
c) optionally purifying the obtained risperidone salt.

In step a), the acid addition salt of risperidone can be prepared by reacting risperidone base with a suitable acid counterion in suitable solvent. The salt formation reaction typically occurs in a single suitable solvent or mixture thereof, although a mixed phase system can be employed like solid-liquid slurry, etc., wherein one or more reactants is not fully soluble in the liquid phase.

A suitable acid counterion is one that is sufficiently reactive to react with the risperidone base to form a salt. The salt formation reaction is generally carried out at a temperature of about 0° C. to reflux temperature of the solvent system. Preferably, the solvent is in amount of from about 1 to about 40 ml per gram of risperidone base.

Wherein, the suitable solvent includes, but are not limited to water, methanol, ethanol, n-butanol, isopropanol, iso-butanol, dimethylformamide, tetrahydrofuran, acetone, benzene, ethyl methyl ketone, acetonitrile, toluene, dimethyl sulfoxide, chloroform or ethyl acetate.

Further, the salt formation reaction can be carried out by combining the solution of risperidone base in first solvent with solution of an acid counter ion prepared in second solvent. Wherein, the first solvent and second solvent can be a different or same.

The amount of the acid counterion used in the process of making risperidone salt is not particularly limited but should advantageously be at least an equivalent amount. For example, for a di-salt at least two moles of acid counterion for each mole of risperidone base should be provided. While less than an equivalent amount of acid counterion can be used, a slight or even substantial excess of the acid counterion is normally preferred.

In step b), after a short period of stirring of the reaction mixture obtained in step a), a solid comprising the risperidone acid addition salt precipitates either spontaneously or after addition of a contra solvent. In a few cases, it may be necessary to cool the solution on an ice bath, or to reduce the solution's volume. The obtained solid, generally crystals, is then filtered off, washed with suitable solvent and dried, preferably in vacuo.

After the risperidone acid addition salt is precipitated it can be isolated by known techniques such as filtration.

In step c), an isolated risperidone acid addition salt may contain some impurities and may be purified into the desired degree of purity by various methods. For instance, it may be recrystallized from a suitable solvent, optionally after treatment with a suitable adsorption material, e.g. with activated charcoal. Suitable solvents include water, methanol, ethanol, n-butanol, isopropanol, iso-butanol, dimethylformamide, tetrahydrofuran, acetone, benzene, ethyl methyl ketone, acetonitrile, toluene, dimethyl sulfoxide, chloroform, ethyl acetate or mixture thereof.

In another aspect, the present invention also provides novel Risperidone hemipamoate.

The present invention further encompasses a process for the preparation of risperidone hemipamoate, which comprises:
a) reacting risperidone with pamoic acid counterion in suitable solvent to form a risperidone salt;
b) removing said suitable solvent, thereby isolating risperidone hemipamoate; and
c) optionally purifying the obtained risperidone hemipamoate.

Risperidone hemipamoate can be prepared in analogous manner as described herein above for other acid addition salt of risperidone.

The present invention also provide crystalline Form T1 of Risperidone hemipamoate characterized by a powder X-ray diffraction pattern having characteristic peaks at about 6.51, 7.26, 9.26, 9.81, 13.55, 16.00, 19.52, 20.82 & 23.6±0.2 degree two theta, which is substantially in accordance with FIG. 1.

The present invention provides a process for the preparation of crystalline form T1 of Risperidone hemipamoate comprises;
a) providing solution of risperidone in methanol;
b) reacting above solution of step a) with pamoic acid solution prepared in suitable solvent; and
c) isolating risperidone hemipamoate crystalline Form-1.

The present invention also provide crystalline Form T2 of Risperidone hemipamoate characterized by a powder X-ray diffraction pattern having characteristic peaks at about 5.24, 5.94, 6.92, 8.81, 15.50, 16.23, 17.68, 18.19, 21.84 & 22.21±0.2 degree two theta, which is substantially in accordance with FIG. 2.

The present invention provides a process for the preparation of crystalline form T2 of Risperidone hemipamoate comprises;
a) providing solution of risperidone in ethanol;
b) reacting the above solution of step a) with pamoic acid solution prepared in suitable solvent; and
c) isolating risperidone hemipamoate crystalline Form-T2.

The suitable solvent for the preparation of pamoic acid solution is same solvent as mentioned herein above and more preferably dimethyl formamide.

In another aspect, the present invention provides pharmaceutical compositions comprising a therapeutically effective amount of an acid addition salt of the risperidone or mixtures thereof according to the present invention, and one or more pharmaceutically acceptable excipients.

The pharmaceutical compositions may be formulated as: solid oral dosage forms such as, but not limited to, powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the form of immediate release, delayed release or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared by direct blending, dry granulation or wet granulation or by extrusion and spheronization. Compositions may be presented as uncoated, film coated, sugar coated, powder coated, enteric coated or modified release coated. Compositions of the present invention may further comprise one or more pharmaceutically acceptable excipients.

Pharmaceutically acceptable excipients that find use in the formulations include, but are not limited to: diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, polyvinyl pyrrolidone, hydroxypropyl cellulose, hydroxypropyl methylcellulose, pregelatinized starch and the like; disintegrants such as starch, sodium starch glycolate, pregelatinized starch, crospovidone, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants such as polysorbate; complex forming agents such as various grades of cyclodextrin, resins; release rate controlling agents such as hydroxypropyl cellulose, hydroxymethyl cellulose, hydroxypropyl methylcellulose, ethyl cellulose, methyl cellulose, various grades of methyl methacrylates, waxes and the like. Other pharmaceutically acceptable excipients that are of use include but are not limited to film formers, plasticizers, colorants, flavoring agents, sweeteners, viscosity enhancers, preservatives, antioxidants and the like.

The present invention provides a long acting formulation comprising a therapeutically effective amount of risperidone hemipamoate or polymorphic form or mixtures thereof and suitable vehicle for injection with duration of drug release from about 7 days to 6 months, preferably 7 days to 1 month, more preferably 7 days to 21 days.

The suitable vehicle according to present invention is selected from biocompatible vehicle or oily vehicle or buffered aqueous vehicle.

A "biocompatible vehicle" according to the present invention may include any pharmaceutically acceptable polymer that can be combined with a solvent to provide a vehicle that is miscible with water, single-phase, suitable for creating and maintaining drug suspension, and capable of providing a stable drug formulation.

Pharmaceutically acceptable polymer is selected from but not limited to sodium carboxymethyl cellulose (CMC), Hydroxypropylmethyl Cellulose, sodium alginate, poloxamer, polyethylene glycol or pectin.

The solvent included in a vehicle according to the present invention includes any solvent that is pharmaceutically acceptable and can be combined with a suitable polymer to provide a vehicle that is miscible with an aqueous liquid, single-phase, biocompatible, suitable for creating and maintaining a drug suspension, and capable of providing a stable drug formulation. The suitable examples of solvents that may be used to provide a vehicle according to the present invention include, but are not limited to, glycofurol, tetraglycol, N-methylpyrrolidone, glycerol formal, glycerine, and propylene glycol.

The biocompatible vehicle optionally comprises one or more pharmaceutically acceptable excipients as described herein above.

The suitable buffer according to the present invention is phosphate buffer, acetate buffer, citrate buffer and Tris(hydroxymethyl)aminomethane.

The oily vehicle according to the present invention selected from Ethyl oleate, Medium Chain Triglyceride, peanut oil, sesame oil, soybean oil, safflower bean oil, ethyl oleate and castor oil.

Long acting formulation of other acid addition salt of risperidone prepared according to present invention can be formulated in analogues manner as described herein above for risperidone hemipamoate.

The various embodiments of the invention having thus been generally described and the following examples are for illustrative purposes only and are not intended, nor should they be interpreted to, limit the scope of the invention.

Method and Condition for the Measurement of Powder X-Ray Diffraction Patterns (1) Method of the Measurement X-ray diffraction patterns were measured on each 350-400 mg of the sample of Risperidone hemipamoate in the following conditions.

(2) Condition of Measurement

| Target | Cu |
|---|---|
| Filter | Nickel |
| Voltage | 45 KV |
| Current | 40 mA |
| Slit | DS-1/2, RS 0.02 |
| Scan Speed | 0.16°/Min |
| Range | 2-40° 2θ |
| Step/Sample | 0.008 |

EXAMPLES

Example—1

Preparation of Risperidone Hemipamoate 700 ml of dimethyl formamide and 16.6 gm of pamoic acid were charged in the flask. The reaction mixture was stirred for 10 minutes at 25-30° C. to obtain clear solution. 35 gm Risperidone solution in 1050 ml ethanol was added to the reaction mixture at 25-30° C. The reaction mixture was stirred further for 5 hours at 25-30° C. The solid was filtered off, washed with 70 ml ethyl alcohol and dried under vacuum at 50-55° C. for 12 hours.

Dry weight: 42.10 gm

DSC: 188° C.

1 H NMR in accord with structure (400 MHz, DMSO-d6+ D$_2$O) δ(ppm): 8.22 (2H) s; 8.14-8.16 (2H) d; 8.00-8.03 (2H) d of d; 7.67-7.69 (4H) m; 7.29-7.33 (2H) d of t; 7.14-7.18 (2H) t; 7.05-7.09 (2H) t; 4.77 (2H) s; 3.81 (4H) t; 3.54 (2H) m; 3.16 & 3.74 (12H) m; 2.89-2.91 (4H) m; 2.75-2.78 (4H) t; 2.10-2.15 & 2.36-2.42 (8H) m; 2.28 (6H) s; 1.75-1. (8H) m.

Elemental analysis (wt %) calculated for $C_{69}H_{70}F_2N_8O_{10}$: C, 68.53; H, 5.83; N, 9.27.

Found: C, 68.37; H, 6.00; N, 9.65.

The structural characteristics were also confirmed by BRUKER's SMART APEX Single crystal X-ray CCD Diffractometer.

Example—2

Preparation of Risperidone Camphor Sulfonate 15 ml methanol and 2.8 gm of L (−) camphor sulfonic acid were charged in flask. The reaction mixture was stirred for 10 minutes at 25-30° C. to obtain clear solution. 5 gm Risperidone solution in 80 ml methanol was added to the reaction mixture within 15-20 minutes at 25-30° C. The reaction mixture was stirred for 5 hours and was distilled out completely under vacuum at 50-55° C. 20 ml of acetone was added further and stirred for 10 minutes at 40-45° C. The reaction mixture was cooled to −5 to −10° C. and stirred for 4 hours. The solid was filtered off, washed with 5 ml acetone and dried in vacuo at 50-55° C. for 12 hours.

Dry weight: 5.1 gm

DSC: 120.4° C.

Example—3

Preparation of Risperidone Decanoate 150 ml of ethanol and 5 gm Risperidone were charged in the flask. The reaction mixture was heated at 50-55° C. and stirred for 10 minutes to get clear solution. 2.1 gm decanoic acid solution in 30 ml ethanol was added to the reaction mixture at 40-45° C. The reaction mixture was further cooled to 25-30° C., stirred for 18-20 hours and distilled out completely under vacuum at 50-55° C. The solid was dried under vacuum at 40-45° C.

Dry weight: 5.3 gm

Example—4

The risperidone hemipamoate of example-1 has intrinsic dissolution rates much less than that compared to risperidone alone as disclosed herein below. The intrinsic dissolution rates were determined by preparing discs of sample (50 mg) and performing dissolution by mounting the sample on shaft of dissolution apparatus with help of disc adaptor. The dissolution was performed in phosphate buffer saline, at 37° C. and rotation of 200 rpm. Samples were withdrawn at regular interval and analyzed by high performance liquid chromatography. The intrinsic dissolution rate was calculated as amount of drug (equivalent to risperidone) dissolved per unit area per unit time.

TABLE

Intrinsic dissolution rate

| Sr. No. | Sample | Intrinsic dissolution rate (mg/cm$^2$/h) |
|---|---|---|
| 1 | Risperidone | 1.89 |
| 2 | Risperidone hemipamoate | 0.49 |

Example—5

Preparation of Crystalline Form-T1 of Risperidone Hemipamoate 3000 ml Methanol and 100 gm Risperidone were charged in the flask. The reaction mixture was stirred for 10 minutes at 25-30° C. The reaction mixture was heated to 70-75° C. Pamoic acid solution (47.33 gm Pamoic acid dissolved in 500 ml DMF at 70-75° C.) added into reaction mass at 70-75° C. within 1 hrs. Reaction mass was stirred at 70-75° C. for 2 hrs. Reaction mass was cooled to 25-30° C. Reaction mass was stirred at 25-30° C. for 2 hrs. Product was filter under vacuum at 25-30° C. Wet solid slurry washed with 1000 ml Methanol at 25-30° C. Suck dried material under vacuum for 30-40 mins. (Wet wt: 225 gm). Wet solid dried in ATD at 70-75° C. for 15-20 hrs.

Dry weight: 127 gm
DSC: 183.95° C.

Example—6

Preparation of Crystalline Form-T1 of Risperidone Hemipamoate 47.33 gm Pamoic acid and 500 ml DMF were charged in the flask. The reaction mixture was stirred for 10 minutes at 25-30° C. The reaction mixture was heated to 70-75° C. Reaction mixture was stirred at 70-75° C. for 15-20 mins. Risperidone solution (100 gm Risperidone dissolved in 3000 ml Methanol at 40-45° C.) added into reaction mass at 70-75° C. within 1 hrs. Reaction mass was stirred at 70-75° C. for 2 hrs. Reaction mass was cooled to 25-30° C. Reaction mass was stirred at 25-30° C. for 2 hrs. Product was filtered and wet solid washed with 1200 ml Methanol. Suck dried under vacuum for 30-40 mins. (Wet wt: 225 gm). Wet solid dried in ATD at 70-75° C. for 15-20 hrs.

Dry weight: 128 gms
DSC: 188.56° C.

Example—7

Preparation of Crystalline Form-T2 of Risperidone Hemipamoate 16.6 gm Pamoic acid and 700 ml DMF were charged in the flask. The reaction mixture was stirred for 10 mins at 25-30° C. Added Risperidone solution (35 gms Risperidone dissolved in 1050 ml Ethanol) into reaction mass at 25-30° C. Reaction mass was stirred at 25-30° C. for 5 hrs. Filter the product and washed with 70 ml Ethanol (Wet wt: 46 gms). Wet solid dried in VTD at 50-55° C. for 10-12 hrs.

Dry weight: 42.1 gms
DSC: 188.91° C.

Example—8

Composition

| Formulation | Ingredients | Quantity |
|---|---|---|
| I | Risperidone base | 36 mg |
|  | Diluent | q.s. to 1 ml |
| II | Risperidone Pamoate | 70 mg |
|  | Diluent | q.s. to 1 ml |
| III | Risperidone Hemipamoate | 53 mg |
|  | Diluent | q.s. to 1 ml |

Diluent Composition:

| Sr. No. | Materials | Qty. |
|---|---|---|
| 1 | Sodium CMC (Blanose 7LF) | 9 mg |
| 2 | Tween 80 | 0.25 mg |
| 3 | Mannitol | 45 mg |
| 4 | WFI | q.s. to 1 ml |

Procedure for Preparation of Suspension:
1. Required quantity of API weighed & taken in glass beaker.
2. Diluent was added to it & stirred with glass rod to ensure proper wetting of API.
3. Above suspension was homogenized using high speed homogenizer/high pressure homogenizer to achieve desired particle size distribution and uniform dispersion of API.

pK Study in Wistar Rats

A comparative evaluation of pharmacokinetic profile of Risperidone, Rispridone pamoate and Risperidone hemipamoate was carried out in male wistar rats. Aqueous suspension formulations of Risperidone base, Pamoate and hemipamoate salt containing 3.6 mg equivalent risperidone base were administered through intramuscular route. Each group (N=5) was administered a single dose. Blood samples were withdrawn at predefined time interval for measurement of Risperidone and 9-hydroxyrisperidone.

| Group | Drug | Dose | Dose volume |
|-------|------|------|-------------|
| I | Risperidone | 3.6 mg | 0.1 ml |
| II | Risperidone pamoate | 7.0 mg | 0.1 ml |
| III | Risperidone hemipamoate | 5.3 mg | 0.1 ml |

The comparative data as disclosed in figure-3 indicates that both salts i.e. risperidone Pamoate and risperidone hemipamoate absorbed rapidly, however exposure remains sustained for longer duration in case of risperidone hemipamoate as compared to risperidone pamoate. Further, the plasma level of risperidone Pamoate salt falls quickly, whereas in case of risperidone hemipamoate it sustains for long duration comparatively and hence risperidone hemipamoate is more efficacious than pamoate salt.

The invention claimed is:

1. A compound which is Risperidone hemipamoate.

2. Risperidone hemipamoate according to claim 1 in crystalline form T1 characterized by a powder X-ray diffraction pattern having characteristic peaks at about 6.51, 7.26, 9.26, 9.81, 13.55, 16.00, 19.52, 20.82 and 23.6±0.2 degree two theta, which is substantially in accordance with FIG. 1.

3. A process for the preparation of risperidone hemipamoate in crystalline form T1 according to claim 2, comprises:
   a) providing solution of risperidone in methanol;
   b) reacting above solution of step a) with pamoic acid solution prepared in suitable solvent; and
   c) isolating risperidone hemipamoate crystalline Form-T1.

4. Risperidone hemipamoate according to claim 1 in crystalline form T2 characterized by a powder X-ray diffraction pattern having characteristic peaks at about 5.24, 5.94, 6.92, 8.81, 15.50, 16.23, 17.68, 18.19, 21.84 and 22.21±0.2 degree two theta, which is substantially in accordance with FIG. 2.

5. A process for the preparation of risperidone hemipamoate in crystalline form T2 according to claim 4, comprises:
   a) providing solution of risperidone in ethanol;
   b) reacting the above solution of step a) with pamoic acid solution prepared in suitable solvent; and
   c) isolating risperidone hemipamoate crystalline Form-T2.

6. The process according to claim 5, wherein suitable solvent is selected from water, methanol, ethanol, n-butanol, isopropanol, iso-butanol, dimethylformamide, tetrahydrofuran, acetone, benzene, ethyl methyl ketone, acetonitrile, toluene, dimethyl sulfoxide, chloroform and ethylacetate.

7. A pharmaceutical composition comprising a therapeutically effective amount of risperidone hemipamoate according to claim 1 and one or more pharmaceutically acceptable excipients.

8. A long acting formulation comprising a therapeutically effective amount of risperidone hemipamoate or mixtures thereof and suitable vehicle for injection.

9. The long acting formulation according to claim 8, wherein vehicle is selected from biocompatible vehicle or oily vehicle or buffered aqueous vehicle.

10. The long acting formulation according to claim 8, wherein duration of drug release is about 7 days to 1 month.

11. The long acting formulation according to claim 8, wherein risperidone hemipamoate is in crystalline Form T1 or T2.

12. The process according to claim 3, wherein suitable solvent is selected from water, methanol, ethanol, n-butanol, isopropanol, iso-butanol, dimethylformamide, tetrahydrofuran, acetone, benzene, ethyl methyl ketone, acetonitrile, toluene, dimethylsulfoxide, chloroform and ethyl acetate.

* * * * *